US006605447B2

(12) United States Patent
Weiss et al.

(10) Patent No.: US 6,605,447 B2
(45) Date of Patent: Aug. 12, 2003

(54) METHODS AND MEANS OF DETECTING NITRIC OXIDE SYNTHASE

(75) Inventors: Robert M. Weiss, North Haven, CT (US); William C. Sessa, Madison, CT (US); Marcia A. Wheeler, Branford, CT (US); Shannon D. Smith, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/142,722

(22) PCT Filed: Mar. 14, 1997

(86) PCT No.: PCT/US97/04293

§ 371 (c)(1),
(2), (4) Date: Feb. 25, 1999

(87) PCT Pub. No.: WO97/34014

PCT Pub. Date: Sep. 18, 1997

(65) Prior Publication Data

US 2002/0164658 A1 Nov. 7, 2002

Related U.S. Application Data

(60) Provisional application No. 60/013,470, filed on Mar. 15, 1996.

(51) Int. Cl.$^7$ ................................................. C12Q 1/12
(52) U.S. Cl. .................... 435/37; 435/7.4; 435/189; 435/240.2; 435/1.1; 435/320.1; 435/252.1; 514/546; 514/564; 514/561; 514/645; 514/632; 514/33; 514/930; 514/398; 604/361; 604/152; 604/2
(58) Field of Search .................... 435/37, 7.4, 189, 435/240.2, 252.3, 320.1, 1.1; 514/546, 645, 564, 632, 634, 33, 561, 930, 398, 152, 2; 604/361

(56) References Cited

U.S. PATENT DOCUMENTS

| | | | | |
|---|---|---|---|---|
| 4,096,037 A | * | 6/1978 | Mia .......................... | 195/103.5 |
| 4,631,255 A | * | 12/1986 | Takino et al. ................. | 435/37 |
| 5,246,970 A | * | 9/1993 | Williamson et al. ......... | 514/632 |
| 5,468,236 A | * | 11/1995 | Everhart et al. ............. | 604/361 |
| 5,468,630 A | * | 11/1995 | Billiar et al. ................ | 435/189 |
| 5,552,267 A | * | 9/1996 | Stern et al. ................... | 435/1.1 |
| 5,554,518 A | * | 9/1996 | Bommarius et al. ........ | 435/114 |
| 5,594,032 A | * | 1/1997 | Gonzalez-Cadavid et al. ............. | 514/645 |
| 5,652,255 A | * | 7/1997 | Adams et al. ............... | 514/398 |
| 5,654,152 A | * | 8/1997 | Koyama et al. .............. | 435/6 |
| 5,723,448 A | * | 3/1998 | Gross et al. .................. | 514/33 |
| 5,723,451 A | * | 3/1998 | Mjalli et al. ................. | 514/255 |
| 5,744,340 A | * | 4/1998 | Fossetta et al. ............. | 435/189 |
| 5,759,836 A | * | 6/1998 | Amin et al. ................. | 435/189 |
| 5,766,909 A | * | 6/1998 | Xie et al. .................... | 435/189 |
| 5,789,395 A | * | 8/1998 | Amin et al. ................. | 514/152 |
| 5,830,848 A | * | 11/1998 | Harrison et al. ............. | 514/2 |
| 5,882,908 A | * | 3/1999 | Billiar et al. ............... | 435/189 |
| 5,885,842 A | * | 3/1999 | Lai ............................. | 436/116 |
| 5,919,775 A | * | 7/1999 | Amin et al. ................. | 514/152 |
| 6,133,316 A | * | 10/2000 | .O slashed.stensen et al. ... | 514/565 |
| 6,210,918 B1 | * | 4/2001 | Riemer ........................ | 435/25 |

OTHER PUBLICATIONS

Farrell, AJ et al, Annals of the rheumatic diseases, Nov. 1992, vol. 51(11), pp. 1219–1222.*
Hoyl, CH et al, Journal of Anatomy, Jun. 1996, vol. 188(part 3), pp. 633–544, (abstract only).*
Sakuri, H et al, Journal of Clinical Investigation, Nov. 1995, vol. 96(5), pp. 2357–2363 (abstract only).*
Albina, JE et al, Journal of Immunology, Nov. 1, 1995, vol. 155(9), pp. 4391–4406.*
Lee et al, Teratology, vol. 49(6), pp. 452–464, Jun. 1994 (abstract only).*
Wheeler, MA et al, Experimental Biology, vol. 95(part II) Apr. 9–13, 1995, FASEB Journal, vol. 9(4), p. A679.*
Kono, T et al, FASEB Journal, vol. 9(4), pp. A679, abstract 3940, Apr. 1995.*
Kopinsky, KL et al, FASEB Journal, vol. 9(4), p. A679, abstract 3937, Apr. 1995.*
Endoh, M et al, Brain Research, vol. 651(1–2), pp. 92–100, 1994.*
Mittal, C K, Biochemical and Biophysical Research communication, vol. 193(1), pp. 126–132, May 28, 1993.*
Keller, R et al, Biochemical and Biophysical Research Communication, vol. 211(1), Jun. 6, 1995, pp. 183–189.*
Weinberg, JB et al, Blood, vol. 86(3), Aug. 1, 1995, pp. 1184–1195.*
Wildhirt, SM et al, International Journal of Cardiology, vol. 50, pp. 253–261, 1995.*
Ney et al., "Nitrovasodilator–induced inhibition of $LTB_4$ release from human PMN may be mediated by cyclic GMP", *Eiconsanoids* 1990, 3:243–245.
Batra et al., "*Interstitial cystitis*", A.U.A. Update Series 1993, 12:1.
Bryant et al., "Co–Purification of 130 KD Nitric Oxide Synthase And A 22 KD Link Protein From Human Neutrophils", *Biochem. Biophys. Res. Commun.* 1992, 189:558–564.

(List continued on next page.)

Primary Examiner—Lynette R. F. Smith
Assistant Examiner—Ginny Allen Portner
(74) Attorney, Agent, or Firm—Licata & Tyrrell, P.C.

(57) ABSTRACT

Methods for identifying and monitoring increased or decreased levels of inducible nitric oxide synthase in biological samples are provided. A collection device for detecting inducible nitric oxide synthase in biological samples is also provided. Detection of inducible nitric oxide synthase is useful in the diagnosis of inflammatory responses such as infections mediated by bacteria, yeast or viruses, transplant rejection, rheumatoid arthritis, interstitial cystitis and cancer.

2 Claims, No Drawings

OTHER PUBLICATIONS

Cattell et al., "Localization of Inducible Nitric Oxide Synthase In Acute Renal Allograft Rejection In the Rat[1]", *Transplantation* 1994, 58:1399.

Cook, "Factors Influencing the Assay of Creatinine", *Ann. Clin. Biochem.* 1975, 12:219.

Devlin et al., Nitric Oxide Generation, *Transplantation* 1994, 58:592.

Hibbs, J.B. Jr., "Synthesis of nitric oxide from L-arginine: a recently discovered pathway induced by cytokines with antitumor and antimicrobial activity", *Research Immunol.* 1991, 142:565–569.

Ioannidis et al., "Evidence for increased nitric oxide production after liver transplantation in humans[1]", *Transplantation* 1995, 59:1293.

Jorens et al., "Modulation of nitric oxide synthase activity in macrophages", *Mediators of Inflamma.* 1995, 4:75–89.

Lachs et al., "Spectrum Bias in the Evaluation of Diagnostic Tests: Lessons from the Rapid Dipstick Test for Urinary Tract Infection", *Ann. Intern. Med.* 1992, 117:135–40.

Langrehr et al., "Nitric Oxide Production in Host–Versus–Graft and Graft–Versus–Host Reactions in the Rat", *J. Clin. Invest.* 1992, 90:679.

Marletta, M.A. J., "Approaches toward Selective Inhibition of Nitric Oxide Synthase", *Med. Chem.* 1994, 37:1900–1907.

Miles et al., "Nitric oxide synthase in circulating vs. Extravasated polymorphonuclear leukocytes", *J. Leukoc. Biol.* Nov. 1995, 58:616–622.

Nathan, C., "Nitric oxide as a secretory product of mammalian cells", *F.A.S.E.B. J.* 1992, 6:3051.

Nathan, C. and Xie, Q., "Nitric Oxide Synthases: Roles, Tolls, and Controls", *Cell* 1994, 78:915–918.

Riesco, et al., "Nitric oxide–generating system as an autocrine mechanism in human polymorphonuclear leucocytes", *Biochem. J.* (1993) 292, 791–796.

Slot, "Plasma Creatinine Determination", *Scand. J. Clin. Lab. Invest.* 1965, 17:381.

Smith et al., "Nitric oxide synthase: An endogenous source of elevated nitrite in infected urine", *Kidney Int.* 1994, 45:586.

Tanaka et al., "Evaluation of Nitric Oxide During Acute Rejection After Heart Transplantation in Rats", *Transplantation Proc.* 1995, 27:576.

Van Devort et al., "Nitric Oxide Regulates Endotoxin–Induced TNF–α Production by Human Neutrophils[1]", *J. Immunol.* 1994, 152:4102–4108.

Weiss et al., "Nitric Oxide Formation As Predictive Parameter For Acute Graft–Versus–Host Disease After Human Allogeneic Bone Marrow Transplantation[1]", *Transplantation* 1995, 60:1239.

Winlaw et al., "Urinary Nitrate Excretion Is A Noninvasive Indicator of Acute Cardiac Allograft Rejection and Nitric Oxide Production in the Rat[1]", *Transplantation* 1994, 58:1031.

Wright et al., "Generation of Nitric Oxide By Human Neutrophils", *Biochem. Biophys. Res. Commun.* 1989, 160:813–819.

Yan et al., "Human Polymorphonuclear Leukoctyes Lack Detectable Nitric Oxide Synthase Activitiy[1]", *J. Immunol.* 1994, 153:1825–1834.

Yang et al., "Induction of Myocardial Nitric Oxide Synthase by Cardiac Allograft Rejection", *J. Clin. Invest.* 1994, 94:714.

\* cited by examiner

SEQUENCE LISTING

```
<160> NUMBER OF SEQ ID NOS:  9

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:  Synthetic

<400> SEQUENCE: 1
actccctcgt ctcactcagg ag                                             22

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:  Synthetic

<400> SEQUENCE: 2
ctggcccagc atcgagctca ctccgcc                                        27

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:  Synthetic

<400> SEQUENCE: 3
cacctttgat gaggggac                                                  18

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence:  Synthetic
```

```
<400> SEQUENCE: 4
agttctgacc tacg                                                    14

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:  Synthetic

<400> SEQUENCE: 5
gtgatggcga agcgagtgaa g                                            21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:  Synthetic

<400> SEQUENCE: 6
ccgagcccga acacagaac                                               19

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:  Synthetic

<400> SEQUENCE: 7
agcgggaaat cgtgcgtg                                                18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:  Synthetic

<400> SEQUENCE: 8
cagggtacat ggtggtgcc                                               19

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence:  Synthetic

<400> SEQUENCE: 9

Tyr Arg Ala Ser Leu Glu Met Ser Ala Leu
  1               5                  10
```

METHODS AND MEANS OF DETECTING NITRIC OXIDE SYNTHASE

This application claims priority to International Application Number PCT/US97/04293, published Sep. 18, 1997, which is a conversion of provisional Application No. 60/013,470, filed Mar. 15, 1996.

INTRODUCTION

This invention was made in the course of research sponsored by the National Institutes of Health, grants DK38311 and DK47548. The U.S. Government may have certain rights in this invention.

FIELD OF THE INVENTION

The present invention provides methods and means for identifying and monitoring increased or decreased levels of inducible nitric oxide synthase in biological samples. Nitric oxide synthase activity is elevated in the inflammatory response resulting from several diseases or conditions, including, but not limited to, bacterial infections including urogenital tract infections and bacterially related sepsis, organ transplant rejection and cancer. Nitric oxide synthase activity is decreased in urine of patients with interstitial cystitis.

BACKGROUND OF THE INVENTION

One of the most common bacterial infections in humans is that of the urinary tract. Patients who need rapid diagnosis of urinary tract infections (UTIs) include premature newborn infants, prepubertal girls and young boys, sexually active women, elderly males and females, pre-operative patients, patients with chronic disease, patients with neurological disorders, patients with genitourinary congenital disorders including urethral valves and reflux, patients with sickle cell disease, patients with renal disease and polycystic kidney disease, patients having undergone renal transplantation and pregnant patients. The diagnosis of UTI in the elderly and in infants, in particular, is difficult because of different signs and symptoms and the inability to communicate, respectively. Failure to diagnose UTIs can lead to urosepsis, emphysematous cystitis and scarring.

Accordingly, there is a need for a rapid, cost effective, sensitive test for UTI. While a definitive diagnosis of urinary tract infections can be obtained by microbial culturing, this test is costly and results from the culture can take up to 48 hours to obtain. Newer technologies involving bacterial antibodies offer no clear advantages over culturing techniques. Studies have confirmed a direct relationship between urine nitrite and urinary tract infections. Accordingly, the Griess reagent which detects nitrite is commonly employed in a dipstick to screen urine for microorganisms. Leukocyte esterase dipstick tests are also used routinely for the rapid diagnosis of urinary tract infections (UTIs). However, these tests have been found to have different sensitivities and specificities for patients with different clinical manifestations. For example, Lachs et al. reported that this dipstick test for urinary tract infection was highly sensitive in patients with a high prior probability of infection but insensitive in patients with a low prior probability of infection (Lachs et al., Ann. Intern. Med. 1992, 117:135–40). Accordingly, as taught by Dr. Martin F. Shapiro in the commentary to this study, the dipstick test for urinary tract infection lacks sensitivity precisely in those patients for whom an effective diagnostic test would be most useful; patients with vague symptoms for whom the diagnosis is not clear. It has been estimated that the current dipstick technologies detect only approximately 50% of UTIs.

Diagnosis of transplant rejection is currently performed by evaluating symptoms along with changes in creatinine levels and by performing renal biopsies. Failure to diagnose acute rejection, which is the most common cause of loss of renal grafts, leads to longer hospital stays and higher medical costs.

Interstitial cystitis is a challenging medical problem because it is fundamentally a diagnosis of exclusion and because it is difficult to treat. Possible etiologies for interstitial cystitis include a viral or bacterial infection, lymphatic obstruction, deficiency of the bladder glycosaminoglycan layer, a pathologic substance in the urine, mast cell infiltration, or an alteration in the sensory nervous system (Batra et al., Interstitial Cystitis A.U.A. Update Series 1993, 12:1).

Nitric oxide synthase (NOS) is an enzyme found in a variety of mammalian tissues including neurons, macrophages and neutrophils. This enzyme converts L-arginine to nitric oxide and citrulline (Nathan, C., F.A.S.E.B. J. 1992, 6:3051). Isoforms of NOS have been characterized as Ca++ dependent and Ca++ independent enzymes in rodents (Nathan, C. and Xie, Q., Cell 1994, 78:915–918). In rodent macrophages and neutrophils, the Ca++ independent form, also referred to as inducible NOS (iNOS) produces large quantities of nitric oxide (NO) that can modulate immune, inflammatory and cardiovascular responses (Nathan, C. and Xie, Q., Cell 1994, 78:915–918 and Hibbs, J. B. Jr., Research Immunol. 1991, 142:565–569). In urine and plasma from rats, iNOS expression and elevated nitrite and nitrate levels are associated with rat cardiac and renal allograft rejection (Tanaka et al., Transplantation Proc. 1995, 27:576; Langrehr et al., J. Clin. Invest. 1992, 90:679; Cattell et al., Transplantation 1994, 58:1399; Yang et al., J. Clin. Invest. 1994, 94:714; Winlaw et al., Transplantation 1994, 58:1031; and Stevens et al., Transplant Proc. 1994, 58:1031). The Ca++ independent form is also activated as part of the host defense mechanism in humans and has been identified in the particulate fraction of the human urine pellet (Smith et al., Kidney Int. 1994, 45:586). Baseline human-urinary-particulate NOS activity is significantly higher in female urine as compared to male urine. Further, levels of this enzyme have been found to increase dramatically in urinary tract infections in both males and females. In addition, in human liver transplant patients, plasma nitrate (Ioannidis et al., Transplantation 1995, 59:1293) and plasma nitroso-compound levels (Devlin et al., Transplantation 1994, 58:592) have been found to increase with acute liver rejection. After allogeneic and autologous bone marrow transplantation in humans, there is also a significant rise of serum nitrate and nitrite levels preceding the onset of clinical symptoms of graft-versus-host disease (Weiss et al., Transplantation 1995, 60:1239). However, the presence of iNOS in human primary cells has been difficult to demonstrate.

Though much effort has been expended on the development of iNOS selective inhibitors as therapeutic agents (Jorens et al., Mediators of Inflamma. 1995, 4:75–89; Marletta, M. A. J., Med. Chem. 1994, 37:1900–1907), the role of iNOS in human infectious and inflammatory processes is poorly understood. Despite some evidence suggesting the presence of iNOS in human macrophages, NOS in human neutrophils is not well characterized. Early reports indicate that human neutrophils can generate small amounts of NO (Wright et al., Biochem. Biophys. Res. Commun. 1989, 160:813–819) and may contain both a constitutive NOS (Bryant et al., *Biochem. Biophys. Res. Commun.* 1992, 189:558–564) and a NO sensitive guanylyl cyclase (Ney et al., *Eiconsanoids* 1990, 3:243–245 and Van Devort et al., *J. Immunol.* 1994, 152:4102–4108). More recent studies, however, have failed to detect either constitutive or inducible NOS activity (Yan et al., *J. Immunol.* 1994, 153:1825–1834). Highly enriched preparations of extravasated human polymorphonuclear leukocytes were reported to contain no message, protein or iNOS enzymatic activity (Miles et al., *J. Leukoc. Biol.* 1995, 58:616–622).

Accordingly, the role of iNOS in inflammatory and infectious organism mediated disease processes in humans and other mammals needs to be better determined. In the present invention, methods and means of detecting and monitoring iNOS levels and activity are provided. These methods have been found to be useful in identifying and monitoring increased or decreased levels of iNOS in biological samples which is useful in the diagnosis of diseases or conditions including, but not limited to, infections mediated by organisms such as bacteria, yeasts and viruses, sepsis, cancer, rheumatoid arthritis, transplant rejection and interstitial cystitis.

SUMMARY OF THE INVENTION

An object of the present invention is to provide methods of identifying and monitoring increased or decreased levels of inducible nitric oxide synthase and activity in biological samples. Means for detecting and monitoring levels of inducible nitric oxide synthase in biological samples are also provided. The identification and monitoring of increased or decreased levels of inducible nitric oxide synthase is useful in diagnosing a variety of disease processes and conditions including, but not limited to, infections mediated by organisms such as bacteria, yeast and viruses, for example, urinary tract infections, sepsis, organ transplant rejection, cancer, rheumatoid arthritis and interstitial cystitis.

DETAILED DESCRIPTION OF THE INVENTION

Molecular, biochemical and immunocytochemical evidence have now identified iNOS as the major NOS isoform in urinary leukocytes. Elevated levels of iNOS can be readily detected in urine of patients suffering from inflammatory diseases including, but not limited to, bacterially related sepsis, urinary tract infections (UTIs). Further, elevated levels of this isoform of NOS have been observed in kidney transplant rejection. The present invention provides novel methods for the measurement of inducible nitric oxide synthase (iNOS) in biological samples which can be used in the identification and diagnosis of such disease processes. As used herein, "biological sample" means a bodily fluid including, but not limited to urine, peritoneal fluid, vaginal secretions, cerebrospinal fluid, amniotic fluid, synovial fluid, saliva or blood. For example, urine from patients is easily obtained and changes in iNOS activity, message and immunoreactivity in urinary leukocytes or changes in the metabolic products of iNOS enzyme (nitrate and cyclic GMP levels) are determined using the methods of the present invention. Accordingly, methods of the present invention provide a rapid and early means for identifying the potential for development of one of these disease states or conditions and aids in their diagnosis.

Methods can be used individually, for example in the rapid diagnosis of UTI by the NADPH diaphorase assay, or in combination. For example, using the methods of the present invention, septic patients, patients with chronic UTIs and renal transplant patients can now be monitored daily for response to treatment and/or signs of rejection by RT-PCR of iNOS, iNOS activity measurements, and measurements of nitrate and nitrite levels in urine. In addition, the methods of the present invention may be used in conjunction with the determination of other symptoms to aid the physician in making a definitive diagnosis of a particular disease or condition.

Nitric oxide synthase levels in urine may be determined in the present invention using a modified Griess test. Nitric oxide synthase from inflammatory cells in urine catalyzes the transformation of arginine to citrulline and nitric oxide (NO) in an NADPH-dependent reaction. Nitrate is an oxidation product of NO. Gram negative bacteria in urine transform the nitrate to nitrite which reacts with the Griess reagent. Standard Griess reagent strips are routinely used in the diagnosis of urinary tract infections by gram negative bacteria. However, the sensitivity of the urine "dipstick" for nitrite is less than optimal. Further, some gram positive bacteria do not reduce nitrate to nitrite. Consequently, this standard assay is of no use in detecting bacterial infections caused by gram positive bacteria, such as Enterococcus. It has now been found that incubation of urine from a patient with L-arginine for several hours prior to addition of the Griess reagent to the urine significantly increases the sensitivity as compared to the standard Griess reagent strip presently in use. Addition of L-arginine to the assay resulted in a significant increase in nitrite production similar to that resulting from direct addition of nitrate. In contrast, addition of L-arginine to filtered urine samples wherein inflammatory cells were removed did not result in increased nitrite levels. Investigation of nitrite production in urine has revealed that endogenous inflammatory cells contain an enzyme, nitric oxide synthase, which increases urine nitrite. The enzymatic production of nitrate is potentiated by exogenous L-arginine. Nitric oxide synthase converts L-arginine to citrulline and nitric oxide; nitric oxide is in turn oxidized to nitrate and nitrite. Conversion of L-arginine into citrulline was confirmed by thin layer chromatography. Accordingly, the addition of arginine to urine increases inflammatory cell production of nitrite, thus making the urine dipstick a more sensitive early predictor of urinary tract infections. It is believed that the endogenous increase in nitrite production resulting from addition of arginine will also make it possible to detect gram positive bacterial infections with this modified Griess test.

An NADPH diaphorase reaction is also used in the present invention to rapidly detect the presence of NOS colorimetrically in inflammatory cells in the urine. NADPH diaphorase converts nitroblue tetrazolium, in the presence of NADPH, to nitro blue tetrazolium formazen, which is purple in color. The formation of nitro blue tetrazolium formazen is rapid (<2 minutes) and extremely sensitive to the presence of inflammatory cells in the urine. This test has been found to be indicative of urinary tract infections with Candida, gram positive bacteria, and gram negative bacteria.

A comparison of the NADPH diaphorase method of the present invention, the leukocyte esterase dipstick test, and the nitrite dipstick tests currently used in the diagnosis of UTIs to microbiology culture results showed NADPH diaphorase testing to be more specific than leukocyte esterase and more sensitive than nitrite testing in predicting UTIs. Initial comparisons revealed the leukocyte esterase dipstick to give false positive results in 40% (16/40) of the samples and false negative results in 2.5% (1/40) of the samples, while the NADPH diaphorase test gave false positive results in only 3.4% (1/29) of the samples and false negative results in 3.4% (1/29). Further, the false positive test was in a post renal transplant patient and thus, is believed to be predictive of rejection. After evaluating 78 urines, it was found that the NADPH diaphorase test is 91% specific and 96% sensitive in detecting UTIs, while the nitrite dipstick is 95% specific and 82% sensitive and the leukocyte esterase dipstick test is only 67% specific and 95% sensitive. Additional testing in more samples has confirmed these results.

In another aspect of the invention, a collection device for detecting inducible nitric oxide synthase is provided comprising a means for collecting a biological sample and a means for detecting inducible nitric oxide synthase which is incorporated into the collection means. For example, in one embodiment, an NADPH diaphorase assay is incorporated into a collection device such as a diaper or continence-control pad to detect asymptomatic UTIs. In this embodiment, the assay is incorporated into a reaction patch comprising reagents for the assay, including, but not limited to, 4-nitro blue tetrazolium. In populations where the risk of undiagnosed UTIs is high, for example in the elderly and in children with genitourinary tract malformations, this testing provides an inexpensive continuous check for UTIs. For example, if the reaction patch in the diaper or pad on the patient changes color, the patients can begin immediate treatment for UTI. This embodiment is also useful in non-invasively detecting other urogenital bacterial infections such as vaginal infections by detecting iNOS in, for example, vaginal secretions. In another embodiment, the reagents for the NADPH diaphorase assay are incorporated into a dipstick or strip or urine collection cup which changes color upon contact with infected urine. Alternatively, in veterinary applications, the collection device can comprise a bedding or litter material which contains reagents for the NADPH diaphorase assay. In this embodiment, UTIs are detected in an animal such as a cat by a change in color in the bedding or litter following contact with urine from the animal. Additional collection devices in which the NADPH diaphorase assay can be incorporated will be obvious to those of skill in the art upon this disclosure.

Reverse transcription-polymerase chain reaction (RT-PCR) is also used in the present invention to detect transcription activity for iNOS-RNA. RNA extracted from cells obtained from urine or other bodily fluids is used as the message for cDNA formation using specific human inducible nitric oxide synthase primers. For example, RT-PCR was performed using oligonucleotide primers based on human iNOS on cDNA prepared from leukocyte enriched total RNA to molecularly identify the NOS isoform(s) in urine from patients with UTIs. A specific 413 bp fragment was consistently amplified with the human iNOS primers. iNOS primer specific RT-PCR products were found in eight leukocyte esterase and nitrite positive urines with greater than $10^5$ CFU/ml of *E. coli* (n=4), Enterococcus (n=1), Pseudomonas (n=1), Klebsiella (n=1) and Enterobacter (n=1). RT-PCR was also performed with primers based on human endothelial NOS (eNOS) as controls. In the same samples, only a faint RT-PCR product was seen using eNOS primers. DNA sequencing of the PCR products revealed 99.9% nucleotide sequence identity with their respective cloned human cDNAs.

Antibodies targeted against iNOS are also used in the present invention to detect the presence of iNOS. For example, Western blotting of total lysates or 2'5'ADP-Sepharose purified samples isolated from leukocyte enriched fractions obtained from patients with UTIs identified immunoreactive iNOS protein at approximately 130 kDA, identical in Mr to the protein product seen in HEK 293 cells stably transfected with the human hepatocyte iNOS cDNA. No iNOS immunoreactivity was found in leukocyte enriched lysates that are leukocyte positive but nitrite and culture negative, or in 2'5'ADP-Sepharose purified samples prepared from leukocytes from a patient with a UTI after six days of antibiotic treatment. Preabsorption of the antisera with the immunogen peptide (YRASLEMSAL-COOH (SEQ ID NO: 9)) eliminated the iNOS immunoreactivity in the total cell lysate and in ADP-Sepharose fractions as well as in transfected HEK 293 cells. Using a specific eNOS monoclonal antibody and using bovine eNOS expressed in HEK 293 cells as a positive control, eNOS protein was undetectable by Western Blot analysis in 6 samples that were positive for human iNOS either by Western blotting or RT-PCR. As will be obvious to those skilled in the art, other assays for detection of iNOS in biological samples using antibodies targeted against iNOS can also be developed in accordance with well known methods and techniques. Such methods include, but are not limited to, competitive and non-competitive assay systems using techniques such as radioimmunoassays, enzyme linked immunosorbent assays, sandwich immunoassays, and fluorescent immunoassays, to name but a few. Such immunoassays can be embodied in a dipstick, strip or other format.

In an embodiment of the invention, a sandwich enzyme immunoassay can be used. For example, an antibody against iNOS, which may be monoclonal or polyclonal, is adsorbed onto a solid support. iNOS present in the biological sample binds to the antibody and unreacted sample components are removed by washing. An enzyme-conjugated antibody binds to the iNOS captured by the first anti-iNOS antibody and completes the sandwich. After removal of any unbound, labeled antibody by washing, a substrate solution is added. A colored product is formed in proportion to the amount of iNOS present in the sample. The color change can be detected using standard spectrophotometric techniques and the amount of iNOS determined against established standards in accordance with well known techniques.

To evaluate the presence of iNOS in leukocyte enriched fractions from patients with UTIs, CD45 positive leukocytes were sorted by flow cytometry and immunofluorescence microscopy was performed. FACS sorting demonstrate that 86–93% (n=3) of the total fluorescent labeling is found in the CD45 positive peak. CD14, a specific marker for human monocytes/macrophages, labels less that 7% of the cells, indicating that the predominant population of CD45 labeled cells are neutrophils. Phase contrast microscopy indicated that greater than 98% of these cells were neutrophils. Immunocytochemistry on cytospins prepared from CD45 positive cells demonstrates iNOS protein in approximately 80% of the cells, most of which are neutrophils.

In addition, NOS enzyme activity is assessed by measuring NO and its oxidation products, citrulline and cyclic GMP, in biological samples. For example, urinary iNOS activity can be determined by measuring the formation of [$^{14}$C]-L-citrulline from [$^{14}$C]-L-arginine while cyclic GMP levels are determined using an $^{125}$I radioimmunoassay.

Using the methods of the present invention, periodic changes in inducible iNOS activity, iNOS RT-PCR product, nitrate and nitrite, and cytokine IL-2 levels can be monitored, for example, in the urine of renal transplant patients. It has been found that urinary particulate-NOS activity is significantly elevated in transplant patients with rejection or infection (5.3±1.0 and 46.9±14.6 pmol citrulline/min/mg protein, respectively) when compared to NOS activity in transplant patients with decreasing or stable creatinine (Cr) levels and without infection (0.54±0.13 pmol citrulline/min/mg protein). The reverse transcriptase-polymerase chain reaction and product sequencing confirm the presence of iNOS in urine leukocytes from patients with transplant rejection. Nitrate levels are elevated with renal transplant rejection, nitrite levels are elevated in infection, and cGMP levels are elevated with both rejection and infection. IL-2 levels are elevated with renal transplant rejection (17.63±6.83 pg/mg Cr) but not with infection (0.29±0.24 pg/mg Cr) when compared with levels measured the first day after transplantation (0.95±0.41 pg/mg Cr). Quantification of iNOS activity in leukocytes from urine of kidney transplant patients shows that iNOS increases 1.8±0.3 days prior to the manifestation of clinical signs and symptoms of kidney rejection. Accordingly, these detection methods of the present invention can be used to accurately identify transplant rejection at an early stage. Periodic levels of iNOS also can be monitored to ascertain efficacy of treatment for infections such as chronic UTIs or in patients at high risk for sepsis.

Using detection methods of the present invention, it was also found that iNOS activity and average cyclic GMP levels are decreased in urine from female patients with interstitial cystitis. In these studies, female patients with interstitial cystitis had significantly less NOS activity in their urine pellet particulate fractions than female controls or females with UTIs, 2.3±1.0, 14±3.0 and 120.0±10 pmol citrulline formed/minute/mg protein, respectively. Urinary cyclic GMP levels which are known to be increased by activation of guanylyl cyclase by nitric oxide were also significantly lower in patients with interstitial cystitis as compared to female controls and females with UTIs; 0.50±0.06, 0.82±0.14, and 3.72±0.81 $\mu$mol cyclic GMP/gram creatinine. Accordingly, the methods of the present invention can also be used in diagnosing interstitial cystitis based upon detection of decreased levels of iNOS in urine in patients as compared to normal control urine.

As will be obvious to those of skill in the art, in addition to urine, the methods of the present invention can also be used for iNOS quantification in other bodily fluids including, but not limited to, peritoneal fluid, vaginal secretions, cerebrospinal fluid, amniotic fluid, synovial fluid, saliva and blood. Thus, quantification of iNOS levels in these other bodily fluids is useful in the early recognition of infections in, for example, peritoneal-dialysis patients and patients with ascites as well as patients with systemic bacterial infection, thus allowing for early treatment of serious infectious processes. Quantification of iNOS levels in synovial fluid can also be used as an aid in definitively diagnosing rheumatoid arthritis.

The following nonlimiting examples are provided to further illustrate the present invention.

EXAMPLES

Example 1

Modified Griess Assay

Urine Sample Isolation

Urine specimens from symptomatic emergency room and urology clinic patients (n=18) were submitted to the Clinical Microbiology Laboratory at the Yale-New Haven Hospital after routine urinalysis. The majority (87%) were clean-catch midstream specimens; the remainder (13%) were obtained by sterile catheterization. Patients' symptoms included dysuria, frequency, urgency, lower abdominal and flank pain and fever. For the purpose of this study, significant bacteriuria was defined as a colony count of greater than $10^5$ CFU/ml of a clearly predominating microorganism. E. coli grew in sixteen samples, Serratia in one sample and Klebsiella in one sample. Ten control urine specimens were obtained from asymptomatic men and women. Control urine samples were negative by reagent strip urinalysis and had less than five white blood cells per milliliter by microscopic exam. All control urine specimens were clean-catch midstream specimens.

Filtration of Urine

To isolate bacteria from inflammatory cells, urine (3 ml) was filtered through a sterile, non-pyrogenic nylon filter with a 5.0 $\mu$m pore size (Micron Separations Inc., Westboro, Mass.). Bacteria were thus isolated in the filtration specimen while leukocytes remained on top of the filter. Because bacteria may contaminate the leukocyte fraction, only the filtered bacterial samples were used in the Griess nitrite determination.

Griess Reaction

Nitrite concentrations in whole urine and filtered urine samples were determined by the Griess reaction. Nitrite reacts with 1% sulfanilamide in 5% $H_3PO_{4/0.1}$% naphthalene-ethylenediamine dihydrochloride forming a chromophore (pink to dark red color) absorbing at 546 nm. The Griess reaction was performed immediately after receiving the urine samples and was repeated after 37° C. incubation for four and eight hours. The Griess reagent (500 $\mu$l) was added to 100 $\mu$l urine and 400 $\mu$l $H_2O$. Nitrite was quantified using $NaNO_2$ standards (0.1–4.0 $\mu$g/500 $\mu$l $H_2O$).

In addition, a portion of the samples was exposed to either 1.0 mM arginine or 1.0 mM nitrate and incubated for four hours prior to Griess determinations.

Example 2

NADPH Diaphorase Assay

NADPH Diaphorase Assay

Urine (200 $\mu$l) is mixed with 250 $\mu$l of 20 mM Hepes buffer, pH 7.2, 200 $\mu$l of 0.75 mM 4-nitro blue tetrazolium, and 80 $\mu$l of 0.2% Triton X-100. The mixture is then incubated at 37° C. The presence of a deep purple color after one minute of incubation at 37° C. is indicative of a positive test for UTIs. In contrast, initial light pink coloration or a purple coloration after several minutes incubation with the test reagent is not indicative of a positive result.

All reagents used in the assay have been found to be stable individually for at least one month when stored at 4° C. They are mixed on the day of the assay.

Hepes (N-(2-hydroxyethyl)piperazine-N'-(2-ethanesulfonic acid) is prepared as a 20 mM solution and adjusted to pH 7.2 with 1 N NaOH.

4-Nitro blue tetrazolium (BM 1087 479) is prepared in deionized water and stored in a dark bottle.

A 2% solution of Triton X-100 (Scintillation grade, Eastman Kodak Company) is prepared in deionized water.

Comparison of NADPH Diaphorase Assay with Nitrite Dipstick and Leukocyte Esterase Dipstick Tests Seventy-eight urine samples submitted for urine culture to the Yale Microbiology Unit from patients in the Yale New Haven Hospital and outpatients in the emergency room and clinic were screened by the urine nitrite and leukocyte esterase dipstick tests and the NADPH diaphorase test. The urine nitrite and leukocyte esterase dipstick tests were performed in accordance with manufacturer's instructions. The NADPH diaphorase test was performed in accordance with the procedures described herein.

Culture and urinalysis results were recorded two days after NADPH Diaphorase testing. In general, culture results represent >100,000 CFU bacteria. Sources of infection included E. coli, Pseudomonas, Enterococcus, Candida, Staphylococcus, Klebsiella, Corynebacterium, and Gamma Strep.

Example 3

Assay of Nitric Oxide Synthase

Urine which was stored on ice was centrifuged at 1700×g (0° C.) to isolate pellet. The resultant pellet was resuspended in an ice cold [20 mM Hepes (pH 7.2), 1.0 mM DTT] buffer solution containing leupeptin (1.0 mg/500 ml) and 1.0 mg/100 ml of soybean trypsin inhibitor, pepstatin, PMSF, antipain and chymostatin. The resuspended pellet was centrifuged at 1700×g for 20 minutes and then homogenized (10 seconds, at 70% power) in 1 ml ice cold buffer solution using a Polytron PT 10/35 homogenizer equipped with a PTA 7 K1 generator (Brinkmann, Westbury, N.Y.). The homogenate was centrifuged at 27,000×g for 45 minutes at 4° C. The pellet was resuspended in 1.5 ml buffer after isolation of supernatant. Samples were passed over a 1.0 ml column of AG 50W-X8 (Na+–form) to remove endogenous arginine, and eluted with 1.0 ml of the buffer. The effluent was used for the enzyme and protein assays.

Nitric oxide synthase activity was measured as the formation of $^{14}$C-citrulline from $^{14}$C-arginine. The particulate enzyme (150 μl) and 50 μl of buffer (Hepes and protease inhibitors) containing 0.2 μCi of $^{14}$C-arginine, 4 mM NADPH, and 1.0 mM $CaCl_2$ were incubated at 37° C. for 45 minutes. NO synthase inhibitors, when used, were added prior to incubation. The assay was terminated with 1 ml of 20 mM Hepes (pH 5.5) containing 2.0 mM EDTA. The sample was applied to a 1.0 ml column of AG 50W-X8 (Na+ form) and eluted with 1 ml of Hepes (pH 5.5). The column effluent was measured in a liquid scintillation counter. Protein concentrations were measured by the Bio-Rad Protein Assay using bovine gamma-globulin as a standard. Insoluble samples were hydrolyzed in NaOH prior to the protein assay.

Verification of Citrulline Production by Thin Layer Chromatography

After completing the enzyme assay and column separation, thin layer chromatography was performed on samples containing the Hepes buffer solution instead of urine or bacteria, and on particulate fraction samples containing either control urine, infected urine, filtered urine, or E. coli isolated from the Yale-New Haven microbiology laboratory from urine cultures grown on blood and MacConkey agar plates. Post-column-separation samples (50–100 μl) and 10 μl of arginine (1.0 mg/ml) and citrulline (1 mg/ml) were applied to silica-gel plates (Sigma #67F-0538m St. Louis, Mo.) and developed with a chloroform-methanol-ammonium hydroxide-water solvent system (0.5:4.5:2.0:1.0). The Rf values for arginine and citrulline were 0.5 and 0.9, respectively.

Example 4

RT-PCR of iNOS and Endothelial NOS (eNOS) from Neutrophil Enriched Leukocytes Total RNA was isolated from neutrophil enriched pellets using Trisolve reagent (Life Technologies, Inc. Gaithersburg, Md.). Single stranded cDNA was synthesized using oligo dT priming and Superscript II Reverse-Transcriptase (Gibco BRL, Life Technologies, Gaithersburg, Md.). Generalized NOS primers (sense 5'-AC$^T$/$_C$CC$^T$/$_C$GT$^c$/$_T$CA$^c$/$_T$CAGGAG-3' (SEQ ID NO: 1) and antisense 5'-CTG$^G$/$_C$CC$^A$/$_G$C$^A$/$_T$$^C$/$_G$AGCTC$^A$/$_c$TC$^C$/$_G$CC-3' (SEQ ID NO: 2)) were first used to produce PCR amplified products from human iNOS, eNOS and neuronal NOS cDNAs. However, Southern blotting of PCR products from neutrophil enriched pellets detected only human iNOS and eNOS products and not neuronal NOS products. Human iNOS specific primers for subsequent PCR analysis were: sense 5'-CACCTTTGATGAGGGGAC-3' (SEQ ID NO: 3) and antisense 5'-AGTTCTGACCTACG-3' (SEQ ID NO: 4). Human eNOS specific primers were: sense 5'-GTGATGGCGAAGCGAGTGAAG-3' (SEQ ID NO: 5) and antisense 5'-CCGAGCCCGAACACAGAAC-3' (SEQ ID NO: 6) as described by Reiling et al., Eur. J. Immunol. 1994, 24:1941–1944. As a control for cDNA synthesis, β-actin primers (sense 5'-AGCGGGAAATCGTGCGTG-31' (SEQ ID NO: 7) and antisense 5'-CAGGGTACATGGTGGTGCC-3' (SEQ ID NO: 8)) were utilized as also described by Reiling et al. PCR Products were electrophoresed on 1% agarose gels and stained with ethidium bromide. The resultant PCR products were 413 bp for iNOS and 422 bp for eNOS. NOS isoform specific primers did not amplify the other forms of NOS (i.e., iNOS primers did not amplify human eNOS nor neuronal NOS cDNAs).

Example 5

Western Analysis

Laemmli sample buffer was added to total cell lysates, membranes, or 2',5 ADP-Sepharose purified iNOS, and samples were heated to 95° C. for 10 minutes. Proteins were electrophoresed on 7.5% gels by SDS-PAGE, transferred to nitrocellulose and blotted with human iNOS specific polyclonal antisera (1:30,000; Maciejewski et al., J. Clin. Invest. 1995, 96:1085–1092) or eNOS specific monoclonal antibodies (1:1000; Pollock et al., Am. J. Physiol. 1993, 265:C1379-C1387). A goat, anti-rabbit Ig conjugated to horseradish peroxidase (Amersham, Buckinghamshire, UK) was used as a secondary antibody for iNOS and a goat, anti-mouse conjugated to horseradish peroxidase (Amersham, Buckinghamshire, UK) was used as a secondary antibody for eNOS. Immunoreactive proteins were detected with the enhanced chemiluminescence method (Amersham, Buckinghamshire, UK).

Example 6

Leukocyte Isolation and Immunohistochemistry

Cell pellets from fresh nitrite positive, leukocyte esterase positive urines were incubated with CD45 (Anti-HLe-1) monoclonal antibody (Becton Dickinson, San Jose, Calif.) (100 μl antibody/75 μl packed pellet) in PBS containing protease inhibitor cocktail (Boehringer Mannheim, Indianapolis, Ind.) and 0.1% albumin, referred to as PBS A, for 30 minutes at 4° C. The antibody was removed by centrifugation (3 times with PBS A, 700×g, 3 minutes) and cells were incubated with fluorescein isothiocyanate labeled anti-mouse IgG (FITC, 1:150) in PBS A for 30 minutes at 4° C. In control cells, the CD45 antibody was omitted. Cells were sorted by flow cytometry, centrifuged onto slides (1200 rpm, 5 minutes) and fixed with acetone at −20° C. for 10 minutes.

For immunocytochemistry, cells were permeabilized with 0.1Triton X-100 for 3 minutes, extensively washed with PBS A and incubated sequentially with iNOS polyclonal antibody (1:1000) for 2 hours at room temperature, and Texas Red anti-rabbit IgG for 1 hour at room temperature. Cells were washed three times after each incubation. Slides were mounted with Slowfade (Molecular Probes) and photographed using a Nikon Microphot-FXA microscope. The specificity of the iNOS antibody was determined by preabsorption of the antisera with the immunogen peptide (YRASLEMSAL-COOH (SEQ ID NO: 9) and by the lack of staining with the secondary antisera alone.

Example 7

Urinary Nitric Oxide Synthase Activity and Cyclic GMP Levels in Patients with Interstitial Cystitis and UTIs Urine sample isolation Interstitial cystitis urine samples were obtained from patients diagnosed in accordance with established inclusion criteria. These urine samples were clean-catch specimens from the first morning void (31%), sterile catheterization samples obtained prior to cystoscopy (44%), and 12 hour clean catch urine samples (25%).

Infected urine samples were obtained from the emergency room, urologic clinic, or the microbiology laboratory at the Yale-New Haven Hospital after routine urinalysis. The majority of the samples were clean-catch midstream specimens (68%) and the remainder were obtained by sterile catheterization. Significant bacterium was defined as a colony count greater than $10^5$ CFU/ml of a clearly predominant microorganism.

Control urine samples were clean-catch, midstream samples obtained from asymptomatic men and women. Control urine samples were negative by leukocyte and nitrite reagent strip analysis and had fewer than five white blood cells per milliliter by microscopic examination.

Determination of Nitric Oxide Synthase Activity

Nitric oxide synthase activity was determined in accordance with procedures described in Example 3.

Measurement of Urinary Cyclic GMP Levels

Urine specimens were centrifuged (1700×g, 5 minutes) and urine supernatant is stored at −80° C. until assay. Cyclic GMP content was determined in 1:50 or 1:100 dilutions of urine supernatant using an $^{125}$I radioimmunoassay (RIA) (Biomedical Technologies, Stoughton, Mass.). Urine creatinine levels were determined spectrophotometrically using alkaline picrate in accordance with procedures described by Slot, *Scand. J. Clin. Lab. Invest.* 1965, 17:381) and Cook, *Ann. Clin. Biochem.* 1975, 12:219). Results were expressed as the urine cyclic GMP/Cr level ratio. Cyclic GMP/Cr ratios are compared to patients' bladder capacity measured under anesthesia.

What is claimed is:

1. A method of identifying increased levels of inducible nitric oxide synthase in a urine sample to assess the risk of a urinary tract infection comprising:
   (a) contacting a urine sample with a means of detecting inducible nitric oxide synthase in the urine sample, wherein L-arginine is the detection means with which the urine sample is contacted and the L-arginine is added to the urine sample before a Griess test is performed to increase sensitivity of detection of inducible nitric oxide synthase and allowing for detection of lower levels of inducible nitric oxide synthase;
   (b) detecting inducible nitric oxide synthase in the urine sample with a Griess test;
   (c) comparing the amount of inducible nitric oxide synthase in the urine sample with an amount detected in a negative control sample or samples that are clean catch, midstream urine samples from asymptomatic men or women and are negative for leukocytes and nitrites and have fewer than 5 white blood cells per milliliter of urine; and (d) determining the risk of a patient having an elevated amount of inducible nitric oxide synthase in the urine sample as high.

2. A method of monitoring levels of inducible nitric oxide synthase comprising:

(a) collecting periodic urine samples from an individual to be monitored during a period of monitoring;

(b) contacting the periodic urine samples with L-arginine as a means of detecting inducible nitric oxide synthase in the urine sample before a Griess test is performed in order to increase the sensitivity of detection of inducible nitric oxide synthase and allowing for detection of lower levels of inducible nitric oxide synthase;

(c) detecting inducible nitric oxide synthase in the periodic urine samples with a Griess test; and (d) determining any changes in levels of inducible nitric oxide synthase in the urine samples during the period of monitoring.

* * * * *